United States Patent [19]
Pfeiffer et al.

[11] 3,937,655
[45] Feb. 10, 1976

[54] METHOD FOR PREPARING STABLE β-LACTAM-TYPE-ANTIBIOTIC SUSCEPTIBILITY TEST DISCS

[75] Inventors: Ralph R. Pfeiffer; Gary L. Engel, both of Indianapolis, Ind.

[73] Assignee: Eli Lilly and Company, Indianapolis, Ind.

[22] Filed: Apr. 16, 1974

[21] Appl. No.: 461,465

[52] U.S. Cl............................ 195/103.5 R; 195/103
[51] Int. Cl.²........................................... C12K 1/04
[58] Field of Search....................... 195/99, 103.5 R

[56] References Cited
UNITED STATES PATENTS 2,787,581   4/1957   Scherr......................... 195/103.5 R
3,713,985   1/1973   Astle............................ 195/103.5 R Primary Examiner—A. Louis Monacell
Assistant Examiner—C. A. Fan
Attorney, Agent, or Firm—Ralph W. Ernsberger; Everet F. Smith

[57] ABSTRACT

Stable antibiotic susceptibility test discs are prepared by depositing crystals of a β-lactam-type-antibiotic on said discs, said crystals being dispersed in a volatile unreactive non-solvent vehicle, such dispersion being contacted with such discs and the vehicle evaporated therefrom.

13 Claims, No Drawings

METHOD FOR PREPARING STABLE β-LACTAM-TYPE-ANTIBIOTIC SUSCEPTIBILITY TEST DISCS

BACKGROUND OF THE INVENTION

This invention relates to a method for preparing β-lactam-type antibiotic test discs used in a clinical microbiological test procedure.

More specifically, this invention concerns a method for preparing β-lactam-type-antibiotic susceptibility test discs which are significantly more stable to heat and storage than those test discs heretofore available from prior art processes. Such enhanced stability greatly increases the reliability of the microbiological test results obtained when such discs are used to determine the susceptibility of pathological microorganisms to the β-lactam-type-antibiotic contained on such discs.

Antibiotic susceptibility test discs have been used for a number of years to determine qualitatively the susceptibility of various pathological microorganisms to the antibiotic contained on such discs. Bauer A. W., et al. [Bauer A. W., Kirby, W. M. M., Sherris, J. C., and Turch, M., Antibiotic Susceptibility Testing by a Standardized Single Disc Method, Am J. Chem Path., 45, 493, (1966)] described the test procedure wherein such test discs are utilized. Usually, the tests are run in hospital laboratories where facilities are available to run microbiological tests. There are, however, some medical laboratories which are independent of hospitals which have the capability to run such tests.

Antibiotic susceptibility tests are run by inoculating a sterile nutrient agar medium, such as Mueller-Hinton agar, with a properly diluted bacterial suspension prepared from a bacterial isolate. The preparation of the inocula and the inoculation procedure are well known to those skilled in the art. The inoculated agar is allowed to dry for 15 to 20 minutes and an antibiotic susceptibility test disc having a specified amount of antibiotic contained thereon, 30 mcg in the case of cephalothin and 10 international units for penicillin G, is placed on the inoculated agar and gently pressed down with a sterile instrument to assure a uniform contact. The thus prepared sample is incubated at 37°C. for 24 hours. An indication of the susceptibility of the pathological microorganism to the antibiotic contained on the test disc is obtained by observing and measuring the diameter of the surface of the medium surrounding the test disc that is free of microorganism growth. For example, if the inhibition zone surrounding a test disc containing 30 mcg of cephalothin is 14 mm or less in diameter, it is indicated that the microorganism is resistant to cephalothin. If the zone diameter is 18 mm or more, the microorganism is judged to be susceptible to cephalothin. Standards have also been established for other antibiotics which are tested in the same manner. These can be found in the Federal Register.

The susceptibility discs are of clean, white paper and can be of different diameters, one popular size being one quarter inch (6.35 mm) in diameter. The standards call for the paper to weigh 30±4 mg per $cm^2$ and to have an absorbtive capacity for distilled water of about 2-3 times the weight of the paper. The paper shall contain no material which will enhance or inhibit the activity of the antibiotic added to it, and can have no effect on the pH of the agar medium or the antibiotic. One grade of paper that meets all of the specifications is alpha cellulose paper No. 676 which can be obtained from Eaton-Dikeman Company, Mount Holly Springs, Pennsylvania.

In the present commercial process, sheets of paper meeting the above detailed specifications are dipped into a solution of the antibiotic, saturated with such solution and removed therefrom. The saturated sheets are subjected to a mechanical compression to remove a substantial portion of the antibiotic solution leaving an amount of solution calculated to deposit the requisite quantity of antibiotic on each one-quarter inch diameter segment of such paper after the solvent is evaporated therefrom. The compressed sheets are then dried at an appropriate temperature, for example, 90°C. in the case of cephalothin, to remove the solvent therefrom and one-quarter inch diameter discs are die cut from the dried paper.

The procedure outlined above results in the deposit of dry amorphous antibiotic in the amount desired on each disc; 30 mcg in the case of cephalothin.

It was found that β-lactam-type-antibiotic susceptibility test discs prepared by this prior art process are highly unstable to heat and storage, losing as much as two-thirds or more of the antibiotic activity after 90 days storage at 37°C.; over half of which was lost in the first thirty days of the storage. Consequently, in order to assure the stated potency, such discs must be refrigerated in actual hospital practice.

Accordingly, it is an object of this invention to provide β-lactam-type-antibiotic susceptibility test discs that will retain substantially all of the antibiotic activity without requiring refrigeration and, in addition, exhibit significantly improved stability on continued storage at 37°C. for up to 90 days over those susceptibility test discs prepared by the prior art process.

Another object of this invention is to provide a method for preparing antibiotic susceptibility test discs having good stability to heat and storage in that such discs retain substantially all of the antibiotic activity when stored at 37°C. for 30 days.

SUMMARY

It has now been discovered that β-lactam-type-antibiotic susceptibility test discs having the antibiotic deposited thereon as a crystalline substance exhibit no significant loss of antibiotic activity after 30 days storage at 37°C. and retain 85 percent or more of such activity after 90 days at 37°C. The antibiotic crystals are deposited on appropriate paper, from which the susceptibility test discs are die cut, by contacting a dispersion of such crystals in a non-solvent vehicle with paper and evaporating the vehicle therefrom. The dispersion can be sprayed onto the paper or poured thereon in metered streams as the paper is moved continuously below a weir over which the dispersion is flowing, or vice versa.

DESCRIPTION OF THE PREFERRED EMBODIMENTS

It has now been discovered that β-lactam-type-antibiotic susceptibility test discs that are stable to heat and storage can be prepared by depositing crystals of the antibiotic on the paper which is the carrier for the antibiotic, the combination thereof comprising the susceptibility test disc.

The useful method of this invention provides a means for preparing such stable susceptibility test discs in which the β-lactam-type-antibiotic is present thereon in the crystalline state. The novel method for preparing such discs comprises contacting absorbent paper with a metered amount of a dispersion of a crystalline β-lactam-type-antibiotic in a volatile non-solvent vehicle, absorbing such dispersion into such paper, evaporating such vehicle from such paper leaving a deposit of a measured quantity of such antibiotic in the crystalline state per unit area of such paper, and forming individual susceptibility test discs from such paper, such discs having an area wherein the desired amount of β-lactam-type-antibiotic is uniformly and consistently deposited.

Standards for the paper employed for the antibiotic susceptibility test discs are set by the Food and Drug Administration (FDA) and have been published in the Federal Register. The approved paper has a weight of from 26 to 34 mg per cm$^2$, and has the capacity to absorb from about 2 to 3 times its weight of distilled water. In using the weight of the paper as a standard a particular specification for the thickness of the paper was avoided. However, since there are both lower and upper limits on the absorbtive capacity of the paper, the thickness can not vary greatly and generally will be about 1.5 mm. Furthermore, the paper must be clean and white and contain no substance which will inhibit or enhance the activity of the β-lactam-type-antibiotic placed thereon nor affect the pH or act as a buffer. Essentially pure alpha cellulose paper meets these standards. One purveyor of such paper is Eaton-Dikeman Company, Mount Holly Springs, Pa.

The paper can be either in sheets or rolls, and depending upon the device used to contact the paper with the antibiotic dispersion, it is of no consequence which is used.

The crystalline β-lactam-type-antibiotic which is to be placed on the paper from which the test discs are cut should have a particle size such that all particles pass a 100 mesh U.S. screen. In actual practice it is preferred that such particles be of a size that all pass a 200 mesh screen, for the smaller particles mean that there are several times the number of particles in a given weight than if the particles are larger. This means more particles on each test disc which provides greater uniformity of β-lactam-type-antibiotic weight from disc to disc. Moreover, the smaller particles will stay suspended in the dispersion more easily and longer than the larger particles, again promoting the preparation of more uniform β-lactam-type-antibiotic weights on each test disc.

However, such small particles are not required to provide β-lactam-type-antibiotic susceptibility test discs having satisfactorily uniform β-lactam-type-antibiotic contents. Nor is it of any significant benefit in the running of the susceptibility tests to have smaller particles of antibiotic on the discs. When test discs prepared using cephalothin sodium which all passed a 100 mesh U.S. screen, and cephalothin sodium which all passed a 200 mesh U.S. screen were compared in side-by-side susceptibility tests, no difference was discernable in the diameters of the inhibition zones observed after incubating the tests for 24 hours at 37°C.

Hence, the β-lactam-type-antibiotic utilized in the useful method of this invention is reduced to a particle size wherein all pass a 100 mesh U.S. screen. A low energy hammer mill can be employed for this operation. Other means of particle size reduction are known to those skilled in the art.

While all useful β-lactam-type-antibiotics are not now offered commercially on susceptibility test discs, it is possible to prepare such discs from all such antibiotics. β-lactam-type-antibiotics comprise a generic class that embraces all the penicillins and cephalosporins and are characterized by a common nucleus, to wit:

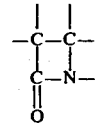

and in the case of the penicillins is fused into a thiazolidine ring and in the case of the cephalosporins is fused into a dihydrothiazine ring. Illustratively, the penicillins are represented by penicillin G, penicillin V, ampicillin, and the like, and the cephalosporins by cephalosporin C, cephalothin, cephaloridine, cephaglycin, cephalexin, cefazolin, cefamandole, cefoxitin, and the like in their pharmaceutically acceptable forms. "In their pharmaceutically acceptable forms" refers to the form in which such antibiotics are administered therapeutically; for example, alkali metal salts thereof such as cephalothin sodium, cefazolin sodium, potassium penicillin G, and the like, the ammonium salt of cefamandole, internal salts such as the zwitter ions of ampicillin, cephaloglycin and cephalexin, and the betaine of cephaloridine. The β-lactam-type-antibiotics are representative and not inclusive of the β-lactam-type-antibiotic agents which are adaptable to this useful method, and the spirit of this invention is intended to embrace all such agents now known and in use and those which, in the further will become useful in combating infections in man and animals.

In one of the operations involved in the useful method described herein the β-lactam-type-antibiotic is dispersed in a volatile non-solvent vehicle. The vehicle is just that, a supportive element used to transport the β-lactam-type-antibiotic onto the paper in a measured amount per unit area. As such it is of no consequence as to what constitutes the vehicle so long as it is volatile, unreactive, and the particular β-lactam-type antibiotic is not soluble therein. The vehicle should boil at or below 100°C at 760 mm of mercury so that it can be easily evaporated from the paper after the β-lactam-type-antibiotic has been transported thereonto. A whole host of materials can be utilized as the vehicle in this operation so long as the above criteria are met. It matters not for the purposes of this process whether these substances are flammable, or even toxic. Prudence will govern the selection of the vehicle and the conditions under which it should be used. Those skilled in the art will know the extent of the explosion and fire-proof facilities they have to work with and the degree of toxicity with which they can safely work in performing the steps of this useful method. For example, in preparing cephalothin sodium susceptibility test discs both isopropanol and chloroform were utilized; the former is relatively flammable but only midly toxic, while the latter is non-flammable but relatively toxic. Those knowledgable about β-lactam-type antibiotics and skilled in their handling will know of the vehicles in which a specific β-lactam-type-antibiotic is not soluble. Inasmuch as the β-lactam-type-antibiotics that are adaptable to this novel method are generally water soluble to a greater or lesser degree, the selection of a non-solvent vehicle having a boiling point at or below 100°C. at 760 mm of mercury presents no problem.

The dispersion of the antibiotic in the volatile nonsolvent vehicle can be effectively accomplished by simply slurrying the crystalline β-lactam-type-antibiotic in the vehicle. The absorbtivity of the paper, the degree of saturation of the paper with the vehicle that is desired, and the concentration of β-lactam-type-antibiotic per unit area of the paper that is required all combine to influence the concentration of the β-lactam-type antibiotic in the dispersion. For example, if the paper which is to be used has an absorbtivity for the non-solvent vehicle of 2 times the weight of the paper and it is desired to saturate the paper to 75 percent of its capacity, with a paper weighing 30 mg per cm$^2$ it is appropriate to provide 45 mg. of such vehicle for every cm$^2$ of paper to be contacted. Taking cephalothin sodium as an example where 30 mcg of cephalothin is to be present on each test disc having a diameter of one-quarter inch (6.35 mm), 90 mcg. of cephalothin is required for each cm$^2$ of paper as each test disc is about one-third square centimeter. With 45 mg. of vehicle to be used and 0.09 mg. of cephalothin to be added to each cm$^2$ of paper, a 0.2 percent dispersion of cephalothin sodium in either isopropanol or chloroform is eminently satisfactory for use in the novel process of this invention. It was found that the most consistently uniform deposits of the β-lactam-type-antibiotic on the paper was accomplished when the paper was saturated with from about 50 to 95 percent of its capacity for the vehicle being utilized. Preferably the degree of saturation should be between about 70 and 90 percent.

Other β-lactam-type-antibiotics and vehicles can be employed in this useful method by following the example outlined immediately above for cephalothin sodium.

Suspending agents which do not alter the pH of the paper or influence the activity of the β-lactam-type-antibiotic can be added to the dispersion to aid in maintaining a homogenous suspension of such antibiotic in the vehicle. Illustrative of such agent are methylcellulose, and polyvinylpyrrolidone, the latter being preferred at a concentration of about 1 percent of the vehicle. The use of such agents also aid in the adhesion of the β-lactam-type-antibiotic particles to the paper after the vehicle is evaporated therefrom. When a suspending agent is employed it is essential that there should be a marriage between the agent and the vehicle; i.e., the agent should either be soluble in the vehicle or solvated by its forming a gel. Otherwise such addition is of no value.

A non-solvent vehicle useful in transporting and depositing penicillin on the paper is isopropanol.

The actual deposit of the β-lactam-type-antibiotic crystals on the paper can best be performed by pouring the β-lactam-type-antibiotic dispersion over a weir in a continuous stream the width of which is essentially the same as the width of the sheet of paper with which the dispersion is being contracted, and at a flow rate coordinated with the velocity with which the weir is moving across the paper, or alternatively, the paper is moving beneath the weir. For example, using paper that is 15 cm wide and with a travel rate of 1 cm per sec beneath the weir, based on the caphalothin sodium illustration hereinbefore detailed, a flow rate over the weir of 0.675 mg. per sec. of a 0.2 percent antibiotic dispersion will deposit 0.09 mg of the β-lactam-type-antibiotic per cm$^2$. Preferably, a stationary weir is employed and the paper which is contacted by the dispersion is moved at a steady rate therebeneath. The weir can be used in conjunction with a speader box, or it can be employed by itself. When the latter is the case the design should be such that the stream of β-lactam-type-antibiotic dispersion is diverted uniformly across the width of the weir where it discharges onto the paper.

As the uniform layer of β-lactam-type-antibiotic dispersion is contacted with the paper, the non-solvent vehicle is rapidly absorbed into the paper leaving the crystals deposited thereon. In this method it is essential that the total vehicle addition to the paper be less than 100 percent of the absorbtive capacity of the paper to assure satisfactory uniformity in the deposit of the β-lactam-type-antibiotic crystals thereon.

The paper which comprises the carrier for the β-lactam-type-antibiotic can also be contacted by dispersions of such antibiotics by spraying the latter onto the paper. This operation can be performed by moving the paper at a uniform controlled rate past a spray nozzle, preferably a fan type nozzle, through which the dispersion is being pumped under pressure. The volume of the flow through the nozzle is correlated with the velocity the paper travels past such nozzle. Preferably the paper is positioned beneath the nozzle and the latter is of a size adapted to provide a pattern of spray that is essentially as wide as the paper moving therebeneath.

Alternatively, the paper can be held stationary and the spray nozzle moved at a predetermined constant rate over the paper. This alternative procedure is highly effective when individual sheets of paper are being processed to provide the β-lactam-type-antibiotic susceptibility test discs.

After the paper has been contacted by the crystalline β-lactam-type-antibiotic dispersion and the non-solvent vehicle absorbed thereon, the paper is subjected to a drying operation to evaporate the vehicle therefrom. This operation can be performed in any of many ways known to those skilled in the art. For example, when the paper is in a continuous roll, the "wetted" paper can be slowly moved through a drying tunnel wherein the vehicle is evaporated away and exhausted to a solvent recovery system, or conveyed to a waste disposal operation. Individual sheets of "wetted" paper can be hung on an endless conveyor traveling through a drying tunnel or such sheets can be placed in an oven or drying cabinet to which heat is applied and a provision made for removing the vehicle vapors and conveying such vapors to an appropriate reclamation or disposal system.

Vacuum can be utilized to speed the vehicle evaporation. The drying temperature should be consistent with the boiling point of the vehicle at the pressure under which the drying is taking place, being no more than a few degrees higher than such point, and in any event such temperature should be no higher than 100°C. Moreover the drying paper should be exposed to the temperature of the drying operation only long enough to complete the removal of all the vehicle from the paper so no decomposition of the antibiotic results.

Whichever vehicle evaporation system is adopted, it should always be kept in mind that the vehicle vapors can be either flammable or toxic or both. Appropriate steps should be taken to protect both personnel and property against these hazards. Means for accomplishing these objectives are well known to those skilled in the art.

The final step in the useful method of this invention is the formation of the individual test discs from the dry paper on which the β-lactam-type-antibiotic has been deposited. This operation is generally accomplished by die cutting the individual discs from the paper utilizing a multiple headed die in a conventional paper trimming press.

While, for the purposes of the instant invention, the size and shape of the discs are not limiting factors, the regulations concerning the use of such discs are specific in this regard. The standards which have been established call for round discs one-quarter inch in diameter. This makes it possible for many manufacturers to prepare discs which can be used interchangeably with confidence that the results will always be comparable. Moreover, while the actual concentration of different antibiotics on the respective test discs varies, each antibiotic is always present in the same amount; the standards being set by the FDA. And in the use of the test discs the inhibition zones will be different for the various antibiotics.

This invention is further illustrated by the following example:

EXAMPLE I

Cephalothin susceptibility test discs were prepared as follows:

1. Cephalothin sodium crystals were hammer milled to a particle size wherein all passed a 100 mesh U.S. screen.
2. The cephalothin sodium crystals so prepared were suspended in isopropanol at a concentration of 2 mg. per ml. (0.2 percent).
3. Approximately 60 microliters of such dispersion was contacted with each square centimeter of sheets of Eaton-Dikenson 676 alpha cellulose paper.
4. The "wet" paper from 3 was placed on stainless steel wire cloth and dried in a circulating air oven at 60°C. and 760 mm of mercury for about 4 min.
5. Individual test discs, each one-quarter inch in diameter were tested for uniformity of caphalothin content by spectrophotometric analysis and ten discs showed less than a 5 percent deviation from the mean.

The test discs prepared as described above were tested for effectiveness in the antibiotic susceptibility test against *Klebsiella pneumoniae*. Discs were placed on the agar with the contacted side both against the agar and away from it. Identical inhibition zones were observed regardless of which side of the disc actually contacted the agar.

Other discs were stored at 37°C. without desiccant. Commercial discs prepared by the prior art process were stored under exactly the same conditions. The results of periodic assays by the disc-plate method are shown in Table 1.

TABLE I

| | Cephalothin Sodium Discs mcg/disc | | | |
|---|---|---|---|---|
| | Init-ial | After 30 days at 37°C. | After 60 days at 37°C. | After 90 days at 37°C. |
| Experimental Discs (crystalline) | 42.4 | 41.5 | 32.2 | 35.5 |
| Commercial Process Discs (amorphous) | 45.0 | 26.0 | 15.0 | 15 |

The disc-plate assay method utilized in this test has an inherent error of ±10 percent. Clearly the cephalothin sodium test discs prepared according to the useful process of the instant invention show significantly greater stability to heat and storage then the commercial test discs prepared by the prior art process.

What is claimed is:

1. A method for preparing stable β-lactam-type-antibiotic susceptibility test discs comprising contacting absorbent paper with a metered amount of a dispersion of a crystalline β-lactam-type-antibiotic in a volatile non-solvent vehicle, absorbing such vehicle into such paper, evaporating such vehicle from such paper leaving a deposit of a measured quantity of such antibiotic per unit area of such paper, and forming test discs from such paper, such discs having an area wherein the desired amount of β-lactam-type-antibiotic is uniformly and consistently deposited.

2. The method of claim 1 wherein said absorbent paper is a clean white paper weighing from 26 to 34 mg. per cm$^2$ and having the capacity to absorb from 2 to 3 times its own weight of distilled water.

3. The method of claim 1 wherein said non-solvent vehicle is an organic solvent in which the β-lactam-type-antibiotic is essentially insoluble, said solvent having a boiling point at or below 100°C. at 760 mm of mercury.

4. The method of claim 1 wherein the β-lactam-type-antibiotic is selected from the group consisting of penicillin G, penicillin V, ampicillin, cephalothin, cephaloridine, cephaloglycin, cephalexin, cefazolin, cefamandole, and cefoxitin in their pharmaceutically acceptable forms.

5. The method of claim 1 wherein the dispersion is comprised of cephalothin sodium suspended in a non-solvent vehicle.

6. The method of claim 1 wherein the dispersion is comprised of cefamandole lithium suspended in a non-solvent vehicle.

7. The method of claim 1 wherein the discs are die cut to a diameter of 6.35 mm (¼ inch).

8. The method of claim 1 wherein the particle size of the crystalline β-lactam-type-antibiotic is such that all pass a 100 mesh U.S. screen.

9. β-lactam-type-antibiotic susceptibility test discs prepared according to the method of claim 1.

10. A method for preparing heat stable β-lactam-type-antibiotic susceptibility test discs comprising the steps of:

a. reducing the crystals of β-lactam-type-antibiotic selected from the class consisting of penicillin G, penicillin V, ampicillin, cephalothin, cephaloridine, cephaloglycin, cephalexin, cef azolin, cef amandole, and cefoxitin in their pharmaceutically acceptable form to a size such that all pass a 100 mesh U.S. screen;

b. dispersing the antibiotic of (a) in a volatile unreactive non-solvent vehicle having a boiling point at or below 100°C. at 760 mm of mercury;

c. uniformly contacting clean white paper weighing from 26 to 34 mg/cm$^2$ and having an absorbtive capacity of 2 to 3 times its own weight of distilled water with the dispersion of (b), the dispersion being contacted with such paper being in an amount that will deposit a susceptibility testrequired quantity of the antibiotic of (a) on each area of such paper corresponding to the area of a susceptibility test disc;

d. evaporating the non-solvent vehicle from the paper of (c); and e. forming individual susceptibility test discs from the paper of (d), each of such discs having an area corresponding to the area of such paper having deposited thereon a susceptibility test required amount of the antibiotic.

11. The method of claim 1 wherein the dispersion is comprised of penicillin G potassium suspended in a non-solvent vehicle.

12. The method of claim 1 wherein the dispersion is comprised of ampicillin suspended in a non-solvent vehicle.

13. The method of claim 1 wherein the dispersion is comprised of cefazolin sodium suspended in a non-solvent vehicle.

* * * * *